United States Patent [19]

Prokop

[11] Patent Number: 5,254,774
[45] Date of Patent: Oct. 19, 1993

[54] PREPARATION OF HEXAFLUOROPROPENE OLIGOMERS

[75] Inventor: Robert A. Prokop, St. Paul, Minn.

[73] Assignee: Minnesota Mining and Manufacturing Company, St. Paul, Minn.

[21] Appl. No.: 997,600

[22] Filed: Dec. 28, 1992

[51] Int. Cl.$^5$ ............... C07C 17/26; C07C 21/18
[52] U.S. Cl. ................... 570/138; 570/126; 570/136
[58] Field of Search ........................... 570/138

[56] References Cited

U.S. PATENT DOCUMENTS

| | | | |
|---|---|---|---|
| 2,918,501 | 12/1959 | Brehm et al. | 260/653.3 |
| 2,983,764 | 5/1961 | Knaack | 570/138 |
| 3,389,187 | 6/1968 | Miller | 570/138 |
| 3,403,191 | 9/1968 | Graham | 570/138 |
| 3,758,618 | 9/1973 | Deem | 570/138 |
| 3,898,293 | 8/1975 | Deem | 570/138 |
| 3,917,724 | 11/1975 | Martini | 260/653.1 |
| 4,016,217 | 4/1977 | Fielding et al. | 570/138 |
| 4,042,638 | 8/1977 | Ozawa et al. | 260/653.1 |
| 4,296,265 | 10/1981 | Ohsaka et al. | 570/138 |
| 4,377,717 | 3/1983 | Anello et al. | 570/172 |
| 4,535,184 | 8/1985 | Middleton | 564/102 |
| 4,780,559 | 10/1988 | Brown et al. | 558/425 |

FOREIGN PATENT DOCUMENTS

| | | | |
|---|---|---|---|
| 117705 | 9/1975 | Japan | 570/138 |
| 87-046528 | 12/1978 | Japan . | |
| 144508 | 12/1978 | Japan | 570/138 |

OTHER PUBLICATIONS

Brown et al., J. Chem. Soc., Chem. Commun. 1985, 672 (1985).
Dmowski et al., J. Fluorine Chem. 9, 94 (1977).
Dresdner et al., J. Org. Chem. 30, 3524 (1965).
Huang et al., J. Organometal. Chem. 218, 164 (1981).
Kobler, H. et al., Justus Liebigs Ann. Chem. (1978), 1937.
Lovelace, A. M., D. A. Rausch, and W. Postelnek, *Aliphatic Fluorine Compounds*, Chapter III (Alkenes and Alkynes), pp. 107–109, Reinhold Publishing Corporation, New York (1958).
Sneed, M. C. and R. C. Brasted, *Comprehensive Inorganic Chemistry*, vol. Six (The Alkali Metals), pp. 61–64, D. Van Nostrand Company, Inc., New York (1957).
*Solubilities*, Fourth Edition, vol. II, pp. 79 and 209, American Chemical Society, Washington, D.C. (1965).
von Halasz et al., Chem. Ber. 106(9), 2950 (1973).

*Primary Examiner*—Joseph E. Evans
*Attorney, Agent, or Firm*—Gary L. Griswold; Walter N. Kirn; Lucy C. Weiss

[57] ABSTRACT

A process for the oligomerization of hexafluoropropene comprises contacting hexafluoropropene with a catalyst or a mixture of catalysts selected from the group consisting of the cyanide, cyanate, and thiocyanate salts of alkali metals, quaternary ammonium, and quaternary phosphonium, in the presence of polar, aprotic solvent, e.g., acetonitrile. The process of the invention is especially useful for selectively preparing hexafluoropropene dimers, e.g., perfluoro-2-methyl-2-pentene and perfluoro-2-methyl-3-pentene, in good yield by the proper choice of solvent and catalyst.

10 Claims, No Drawings

PREPARATION OF HEXAFLUOROPROPENE OLIGOMERS

This invention relates to a process for preparing oligomers, e.g., dimers and trimers, of hexafluoropropene.

Hexafluoropropene oligomers are useful as solvents and as reactive intermediates for the preparation of monomers, surfactants, and other materials such as textile treating agents, paper treating agents, and potting compounds. Hexafluoropropene oligomers have been prepared by both gas-phase and liquid-phase processes involving a variety of catalysts.

Gas-phase hexafluoropropene oligomerization processes are solventless processes which have utilized catalysts such as alkali metal fluorides (see, for example, Dresdner et al., J. Org. Chem. 30, 3524 (1965)), activated carbon (see, for example, U.S. Pat. No. 4,377,717 (Anello et al.)), and alkali metal fluoride supported on activated charcoal or nickel oxide (see, for example, U.S. Pat. No. 4,296,265 (Ohsaka et al.)). These processes involve contacting gaseous hexafluoropropene with the catalyst at elevated temperature.

Liquid-phase hexafluoropropene oligomerization processes have utilized aprotic solvents and catalysts such as metal halides (preferably fluorides and bifluorides) and hydroxides (see, for example, U.S. Pat. No. 2,918,501 (Brehm et al.)), ammonium fluoride (see, for example, Japanese Patent Publication No. 87-046528 (Neos KK)), fluorine-containing amines (see, for example, U.S. Pat. No. 3,917,724 (Martini) and von Halasz et al., Chem. Ber. 106(9), 2950 (1973)), quaternary ammonium salts (see, for example, Brehm et al., supra), pi-bis-(arene)chromium(0) complexes (see, for example, Huang et al., J. Organometal. Chem. 218, 164 (1981)), and tris(disubstituted amino)sulfonium perfluorocarbanion salts (see, for example, U.S. Pat. No. 4,535,184 (Middleton)). These processes involve contacting hexafluoropropene with the catalyst-solvent combination.

U.S. Pat. No. 4,042,638 (Ozawa et al.) and Dmowski et al., J. Fluorine Chem. 9, 94 (1977) teach that dimers or trimers of hexafluoropropene can be selectively obtained in liquid-phase oligomerization processes by the proper choice of solvent and catalyst. These references also disclose the use of crown ethers in combination with halide catalysts to increase the solubility of the catalysts.

U.S. Pat. No. 4,780,559 (Brown et al.) and Brown et al., J. Chem. Soc., Chem. Commun. 1985, 672 (1985) describe a new source of fluoride ion, tetraphenylphosphonium hydrogendifluoride, which can be used to catalyze the oligomerization of olefins such as hexafluoropropene. The latter reference also points out the importance of using dry reagents in such reactions.

Briefly, this invention provides a process for the oligomerization of hexafluoropropene. The process comprises contacting (such as by mixing or otherwise) hexafluoropropene with a catalyst or a mixture of catalysts selected from the group consisting of the cyanide, cyanate, and thiocyanate salts of alkali metals, quaternary ammonium, and quaternary phosphonium in the presence of polar, aprotic solvent (such as acetonitrile), the solvent serving to dissolve or disperse the catalyst(s). The process of the invention is especially useful for selectively preparing hexafluoropropene dimers, e.g., perfluoro-2-methyl-2-pentene and perfluoro-2-methyl-3-pentene, in good yield by the proper choice of solvent and catalyst.

The catalysts used in the process of the invention are inexpensive, commercially available materials, at least some of which also provide solubility advantages (in at least some solvents commonly used for hexafluoropropene oligomerization) over conventional catalysts such as potassium fluoride. For example, 100 grams of anhydrous acetonitrile dissolves 11.31 grams of potassium thiocyanate but dissolves only 0.0036 grams of potassium fluoride at 18° C. (see *Solubilities*, Fourth Edition, Volume II, pages 79 and 209, American Chemical Society, Washington, D.C. (1965)). Such greater catalyst solubility reduces or eliminates any need for the addition of expensive crown ethers as catalyst solubilizing agents (cf. Ozawa et al., supra). Furthermore, the cyanate and thiocyanate salts are not hygroscopic and can therefore generally be used without the need for drying procedures.

Hexafluoropropene can be prepared by methods such as the pyrolysis of fluorine-containing materials, e.g., chlorodifluoromethane, and the decarboxylation of salts of fluorocarboxylic acids (see A. M. Lovelace, D. A. Rausch, and W. Postelnek, *Aliphatic Fluorine Compounds*, Chapter III (Alkenes and Alkynes), pages 107–09, Reinhold Publishing Corporation, New York (1958)). Hexafluoropropene is also commercially available.

Catalysts which can be employed in the process of the invention are quaternary ammonium, quaternary phosphonium, and alkali metal cyanides, cyanates, and thiocyanates, and mixtures thereof. Such catalysts are commercially available but, if desired, can be prepared by methods such as those described by M. C. Sneed and R. C. Brasted in *Comprehensive Inorganic Chemistry*, Volume Six (The Alkali Metals), pages 61–64, D. Van Nostrand Company, Inc., New York (1957), and by H. Kobler et al. in Justus Liebigs Ann. Chem. 1978, 1937. Representative examples of suitable catalysts include the cyanide, cyanate, and thiocyanate salts of lithium, sodium, potassium, tetraalkyl ammonium, and tetraaryl phosphonium, and mixtures of such salts. The potassium salts and mixtures thereof are preferred for use in the process of the invention. Potassium cyanate is most preferred, because it is less toxic and less hygroscopic than potassium cyanide and because, unlike potassium thiocyanate, it generally provides colorless oligomeric product.

Solvents which are utilized in the process of the invention are polar, aprotic solvents. Representative examples of these solvents are acyclic ethers such as diethyl ether, ethylene glycol dimethyl ether, and diethylene glycol dimethyl ether; carboxylic acid esters such as methyl formate, ethyl formate, methyl acetate, diethyl carbonate, propylene carbonate, ethylene carbonate, and butyrolactones; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof. If desired, polar, aprotic solvent can be mixed with nonpolar, aprotic solvent (such as toluene) to modify the distribution of product oligomers or the oligomerization reaction rate. Preferred solvents include dimethyl sulfoxide, N,N-dimethylformamide, ethylene glycol dimethyl ether, diethylene glycol dimethyl ether, acetonitrile, and mixtures thereof, as these solvents enable the preparation of oligomer in good yield. Acetonitrile is most preferred because it can be utilized to selectively and almost quantitatively prepare hexafluoropropene dimer, whereas the use of other solvents generally results in mixtures of dimer and trimer. The ratio of dimer to trimer (and the dimer isomer ratio, i.e., the ratio of perfluoro-2-methyl-2-pentene to perfluoro-2-methyl-3-pentene) in the oligomeric product varies with solvent and catalyst.

The process of the invention can be carried out by combining or mixing catalyst and solvent in a vessel, which can be an open or closed vessel, and which preferably is a sealed, stirred, temperature- and pressure-controlled reactor which is capable of withstanding pressures of up to about 689 kPa (100 psig). The hexafluoropropene is then fed into the catalyst-solvent combination or mixture within the open or closed vessel or, alternatively, is fed into the head space of the closed vessel, and the contents of the vessel is preferably agitated to maximize contact between the catalyst and the hexafluoropropene. Although the catalyst and solvent are typically placed in the vessel prior to addition of the hexafluoropropene, this order of addition of hexafluoropropene, catalyst, and solvent to the vessel is not essential. Crown ethers can be added as catalyst solubilizing agents, if desired, but these are generally not necessary.

The process of the invention can be generally carried out at a temperature in the range of from about −20° C. to about 200° C., preferably from about 0° C. to about 100° C. (depending, e,g., on the reaction rate desired), but lower temperatures can be utilized. Any pressure can be employed depending upon the desired reaction rate, but pressures above atmospheric pressure are preferred. Catalyst is used in an amount sufficient to initiate and sustain the oligomerization reaction, e.g., in an amount ranging from about 0.001% to about 10% by weight of the materials charged. Both the reaction conditions and the proportions of hexafluoropropene, catalyst, and solvent can vary widely. The oligomerization process can be carried out continuously (by continuously feeding hexafluoropropene reactant to the vessel and continuously withdrawing oligomeric product from the vessel), semi-continuously (by continuously feeding reactant and intermittently withdrawing product, or by intermittently feeding reactant and continuously withdrawing product), or batchwise. The continuous mode of operation is preferred for efficiency and ease of operation.

The oligomeric product of the process of the invention is substantially insoluble in the solvent and forms a lower product phase which can be separated from the catalyst-solvent combination or mixture by draining. If desired, the dimeric and trimeric components of the product can then be separated from each other by means such as distillation. The hexafluoropropene oligomeric products are useful as solvents and as reactive intermediates for the preparation of monomers, surfactants, and other materials such as textile treating agents, paper treating agents, and potting compounds.

This invention is further illustrated by the following examples, but the particular materials and amounts thereof recited in these examples, as well as other conditions and details, should not be construed to unduly limit this invention.

EXAMPLES

Example 1

This example describes the oligomerization of hexafluoropropene using potassium thiocyanate as the catalyst and acetonitrile as the solvent.

125 mL of acetonitrile and 10 g of potassium thiocyanate were placed in a 600 mL stirred PARR TM reactor. The reactor was sealed and was attached to a vacuum/pressure manifold. The manifold and the reactor were evacuated to a pressure of 30 mm Hg, and hexafluoropropene (HFP) was then charged to the reactor to give a pressure of 124 kPa (18 psig). The contents of the reactor was stirred at 400 RPM, and heating of the reactor contents was begun by setting the temperature controller at 50° C. HFP was added to the reactor to give a pressure of 503 kPa (73 psig), and an exothermic reaction took place which raised the temperature of the contents of the reactor to 60° C. After the exotherm, the reactor contents were held at a temperature of 50° C., while HFP was continually added to the reactor to maintain a pressure of about 517 kPa (75 psig). Forty minutes after the start of the exotherm, 146 g of HFP had been consumed, and the reaction was terminated by stopping the flow of HFP to the reactor. The reactor and its contents were cooled to room temperature, and the reactor was dismantled. The contents of the reactor was transferred to a separatory funnel and phase separated to give 136 g of a lower fluorocarbon phase which, according to gas chromatography, consisted of 96% HFP dimer, 0% HFP trimer, and 4% unidentified materials. The yield of HFP dimer was 89% (based upon the amount of HFP introduced).

Examples 2–14

The oligomerization of hexafluoropropene was carried out in essentially the manner of Example 1, using various different catalysts and solvents, as shown in Table 1 below. The data of Table 1 shows that other catalysts and other solvents can be used successfully to obtain good yields of hexafluoropropene oligomers in most cases.

TABLE 1

| Example No. | Catalyst (amount) | Temperature (°C.) | Pressure (kPa) | Solvent* (125 mL) | % Yield of Crude Product | % Dimer in Product** | % Trimer in Product |
| --- | --- | --- | --- | --- | --- | --- | --- |
| 2 | KSCN (10 g) | 60 | 544 | DMF | 97 | 36.2 | 59.7 |
| 3 | KSCN (10 g) | 60 | 503 | $CH_3CN$ | 93 | 96.0 | 0.0 |
| 4 | KOCN (10 g) | 50 | 124 | $CH_3CN$ | 96 | 96.0 | 0.7 |
| 5 | KCN (8 g)** | 50 | 427 | $CH_3CN$ | 89 | 96.0 | 2.0 |
| 6 | KOCN (5 g) | 50 | 441 | DMSO | 95 | 30.2 | 67.8 |
| 7 | KOCN (10 g) | 50 | 503 | $CH_3CN$ | 86 | 96.6 | 0.4 |
| 8 | KOCN (10 g) | 50 | 420 | DMSO | 73 | 38.7 | 59.5 |
| 9 | KOCN (10 g) | 50 | 413 | Glyme | 61 | 29.1 | 67.0 |
| 10 | KOCN (10 g) | 50 | 303 | Diglyme | 93 | 89.0 | 8.1 |
| 11 | KOCN (10 g) | 50 | 379 | $CH_3CN$ | 94 | 95.5 | 0.0 |
| 12 | KSCN (10 g) | 50 | 379 | $CH_3CN$ | 92.5 | 94.5 | 0.0 |
| 13 | KOCN (0.5 g) | 50 | 344 | $CH_3CN$ | 85 | 90.7 | 0.0 |

TABLE 1-continued

| Example No. | Catalyst (amount) | Temperature (°C.) | Pressure (kPa) | Solvent* (125 mL) | % Yield of Crude Product | % Dimer in Product** | % Trimer in Product |
|---|---|---|---|---|---|---|---|
| 14 | KOCN (10 g) | 90 | 482 | DMF | 3.4 | 16.9 | 59.5 |

*Solvents:
"DMF" is N, N-dimethylformamide
"DMSO" is dimethyl sulfoxide
"Glyme" is ethylene glycol dimethyl ether
"Diglyme" is diethylene glycol dimethyl ether
**The ratio of the thermodynamic isomer, $(CF_3)_2CF—CF=CF—CF_3$ to the kinetic isomer, $(CF_3)_2C=CF—CF_2CF_3$ in the dimer product was 24:1 for Example 11, 17:1 for Example 12, 112:1 for Example 13, and 6.3:1 for Example 14.
***The KCN used was dried at 180° C. and 20 torr.

Various modifications and alterations of this invention will become apparent to those skilled in the art without departing from the scope and spirit of this invention.

I claim:

1. A process for the oligomerization of hexafluoropropene comprising contacting hexafluoropropene with a catalyst or a mixture of catalysts selected from the group consisting of the cyanide, cyanate, and thiocyanate salts of alkali metals, quaternary ammonium, and quaternary phosphonium, in the presence of polar, aprotic solvent.

2. The process of claim 1 wherein each said catalyst is selected from the group consisting of the cyanide, cyanate, and thiocyanate salts of potassium, sodium, lithium, tetraalkyl ammonium, and tetraaryl phosphonium.

3. The process of claim 1 wherein each said catalyst is selected from the group consisting of the cyanide, cyanate, and thiocyanate salts of potassium.

4. The process of claim 1 wherein said catalyst is potassium cyanate.

5. The process of claim 1 wherein said polar, aprotic solvent is selected from the group consisting of acyclic ethers, carboxylic acid esters, alkyl nitriles, alkyl amides, alkyl sulfoxides, alkyl sulfones, oxazolidones, and mixtures thereof.

6. The process of claim 1 wherein said polar, aprotic solvent is selected from the group consisting of dimethyl sulfoxide, N,N-dimethylformamide, ethylene glycol dimethyl ether, diethylene glycol dimethyl ether, acetonitrile, and mixtures thereof.

7. The process of claim 1 wherein said polar, aprotic solvent is acetonitrile.

8. The process of claim 1 wherein said process further comprises the step of recovering the resulting oligomeric product.

9. The process of claim 8 wherein said process further comprises the step of separating said product into dimeric and trimeric components.

10. A process for the oligomerization of hexafluoropropene comprising contacting hexafluoropropene with a catalyst selected from the group consisting of the cyanide, cyanate, and thiocyanate salts of potassium in the presence of acetonitrile.

* * * * *